(12) United States Patent
Yang et al.

(10) Patent No.: US 10,827,340 B2
(45) Date of Patent: Nov. 3, 2020

(54) EMERGENCY DETERMINATION DEVICE

(71) Applicant: Xandar Kardian, Seoul (KR)

(72) Inventors: Sun Jong Yang, Gangwon-Do (KR); Jeong Woo Choi, Seoul (KR)

(73) Assignee: Xandar Kardian, Seoul (KR)

( * ) Notice: Subject to any disclaimer, the term of this patent is extended or adjusted under 35 U.S.C. 154(b) by 0 days.

(21) Appl. No.: 16/811,131

(22) Filed: Mar. 6, 2020

(65) Prior Publication Data

US 2020/0288294 A1 Sep. 10, 2020

(51) Int. Cl.
*G06F 3/01* (2006.01)
*H04W 4/90* (2018.01)
*H04H 20/59* (2008.01)
*A61B 5/00* (2006.01)
*G06F 3/16* (2006.01)

(52) U.S. Cl.
CPC ............... *H04W 4/90* (2018.02); *A61B 5/002* (2013.01); *G06F 3/017* (2013.01); *G06F 3/167* (2013.01); *H04H 20/59* (2013.01)

(58) Field of Classification Search
CPC .................................. H04W 4/90; G06F 3/017
See application file for complete search history.

(56) References Cited

U.S. PATENT DOCUMENTS

| | | | |
|---|---|---|---|
| 9,736,630 B2 * | 8/2017 | King | G08B 21/0415 |
| 2014/0142403 A1 * | 5/2014 | Brumback | A61B 5/02433 600/324 |
| 2015/0194034 A1 | 7/2015 | Shim et al. | |

FOREIGN PATENT DOCUMENTS

| | | |
|---|---|---|
| JP | H10-155749 A | 6/1998 |
| JP | H11-501241 A | 2/1999 |
| JP | 2000-093398 A | 4/2000 |
| JP | 2014-518666 A | 8/2014 |
| JP | 2015-132963 A | 7/2015 |
| JP | 2018-047140 A | 3/2018 |
| KR | 10-2018-0097403 A | 8/2018 |
| KR | 10-2018-0136770 A | 12/2018 |
| WO | 2004/114184 A1 | 12/2004 |
| WO | 2019/021744 A1 | 1/2019 |

* cited by examiner

*Primary Examiner* — Michael T Vu
(74) *Attorney, Agent, or Firm* — Locke Lord LLP; Scott D. Wofsy

(57) ABSTRACT

The present disclosure provides an emergency determination device. The emergency determination device includes a sensor configured to detect a vital sign of a person and a hand gesture of the person within a predetermined range, and a determiner configured to analyze the vital sign recognized by the sensor, to additionally analyze the hand gesture based on a result obtained by analyzing the vital sign, and to determine whether the emergency occurs, wherein the determiner analyzes the vital sign and determines whether the emergency occurs after the sensor detects a wake-up behavior.

15 Claims, 5 Drawing Sheets

EMERGENCY DETERMINATION DEVICE

CROSS-REFERENCE TO RELATED APPLICATION

This application claims under 35 U.S.C. § 119(a) the benefit of priority to Korean Patent Application No. 10-2019-0026318 filed on Mar. 7, 2019, the entire contents of which are incorporated herein by reference.

BACKGROUND

(a) Technical Field

The present disclosure relates to an emergency determination device for detecting a vital sign of a person and a hand gesture of the person and determining whether an emergency occurs in a person.

(b) Background Art

As healthcare technologies have developed, various devices for enhancing the quality of life have been developed. In addition, electronic devices including a sensor for measuring a vital sign of a person have been developed. A user who uses such an electronic device is capable of measuring information related to a body and recognizing his or her body state using the electronic device. The device measures various vital signs such as heart rate, oxygen saturation, stress, and blood pressure of user using a sensor. The electronic device measures various vital signs of the user using sensing information acquired through the sensor.

While a person sleeps or takes a rest in bed, an emergency may occur in a human body. When a person stays indoor alone, even if an emergency occurs, there is a problem in that there is nobody to help him or her.

CITED REFERENCE

Korean Patent Publication No. 10-2018-0097403 (20180831)

SUMMARY OF THE DISCLOSURE

In one aspect, the present disclosure provides an emergency determination device for detecting the state of a person in real time and automatically recognizing that the person in an emergency.

In another aspect, the present disclosure provides an emergency determination device for identifying whether a symptom detected by analyzing a vital sign corresponds to a mysterious symptom or an emergency, analyzing the vital sign and a hand gesture, and recognizing that the person in the emergency.

When the vital sign measured by the sensor is matched with the information on the mysterious symptom, the determiner may detect the hand gesture and may determine whether the emergency occurs.

For example, when the sensor does not detect the hand gesture matched with a setting condition for a first time, the sensor may repeatedly measure the vital sign.

For example, when the vital sign that is repeatedly measured is continuously matched with the information on the mysterious symptom and the sensor does not detect the hand gesture matched with the setting condition for a second time, the determiner may determine that the emergency occurs, and the second time may be longer than the first time.

For example, when the vital sign measured by the sensor is matched with the information on the emergency, even if the hand gesture is not detected, the determiner may determine that the emergency occurs.

For example, the emergency determination device may further include a communicator configured to transmit a message indicating that the emergency occurs to a predetermined emergency center or urgent center when determining that the emergency occurs.

For example, after the determiner determines that the emergency occurs, the communicator may transmit information on the vital sign of the person to the predetermined emergency center or the urgent center in real time.

For example, the emergency determination device may further include an emergency button configured to indicate that the emergency occurs to the outside, wherein the emergency button may be enabled when the determiner determines a mysterious symptom is generated in the person.

For example, when the sensor detects a sleep behavior, the determiner may determine that the emergency does not occur in the person and may stop analyzing the vital sign of the person and analyzing the hand gesture.

BRIEF DESCRIPTION OF THE DRAWINGS

The above and other features of the present disclosure will now be described in detail with reference to certain exemplary embodiments thereof illustrated in the accompanying drawings which are given hereinbelow by way of illustration only, and thus are not limitative of the present disclosure, and wherein.

DETAILED DESCRIPTION

The attached drawings for illustrating exemplary embodiments of the present disclosure are referred to in order to gain a sufficient understanding of the present disclosure, the merits thereof, and the objectives accomplished by the implementation of the present disclosure. The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. Meanwhile, the terminology used herein is for the purpose of describing particular embodiments and is not intended to limit the invention. Like reference numerals in the drawings denote like elements.

Embodiments described in the specification will be described with reference to cross-sectional views and/or plan views that are ideal exemplary drawings of the present disclosure. Blocks shown in the drawings are functionally separated, and in this regard, one component may be embodied by combining a plurality of blocks. That is, a plurality of blocks may be illustrated depending on functions thereof in an illustrated block diagram. Regions exemplified in the drawings have schematic attributes, and shapes of the regions exemplified in the drawings are used to exemplify a specific shape of a region of a device rather than limiting the scope of the invention.

Figure 1:
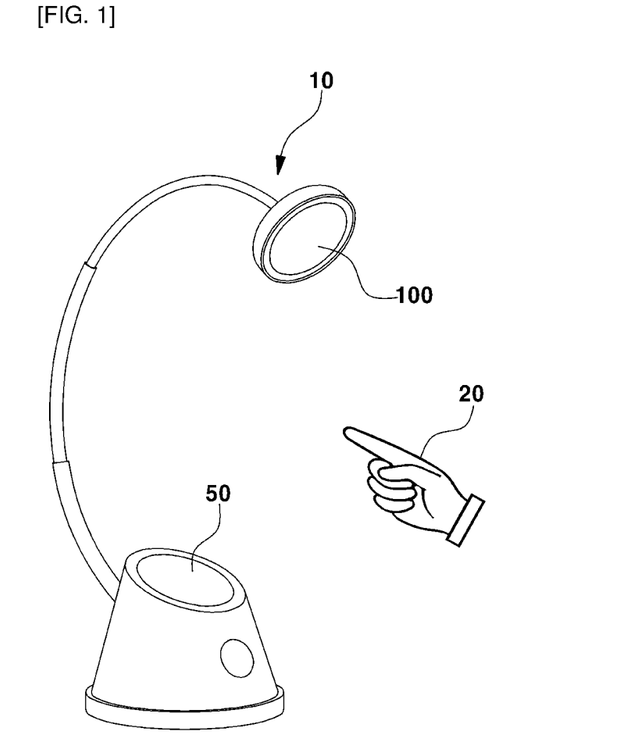
FIG. 1 is a diagram showing an emergency determination device according to an embodiment of the present disclosure.
Figure 2:
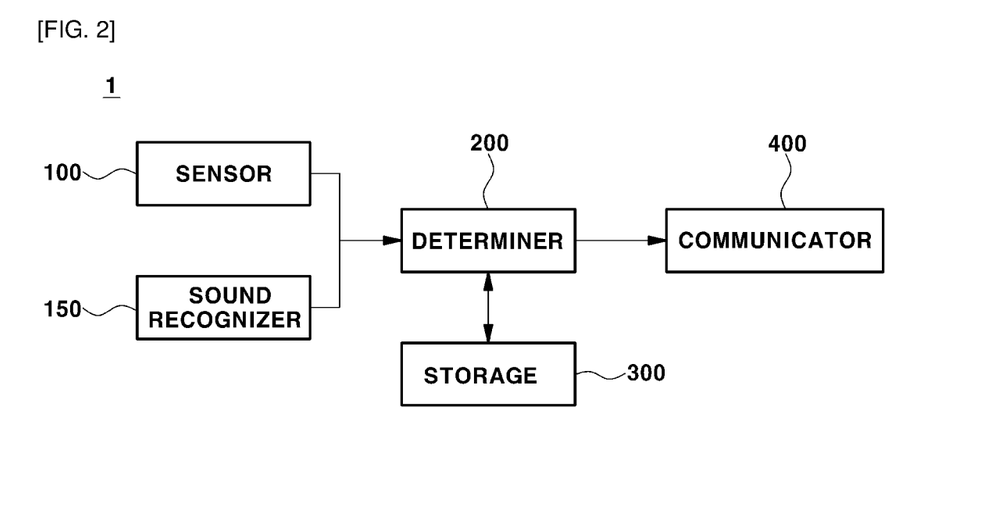
FIG. 2 is a block diagram showing an emergency determination device according to an embodiment of the present disclosure.

FIG. 1 is a diagram showing an emergency determination device according to an embodiment of the present disclosure. FIG. 2 is a block diagram showing an emergency determination device according to an embodiment of the present disclosure.

Referring to FIGS. 1 and 2, an emergency determination device 1 may include a sensor 100, a sound recognizer 150, a determiner 200, a storage 300, and a communicator 400. The emergency determination device 1 may be components included in a housing 10 or an algorithm. The housing 10 may include an emergency button 50 and the sensor 100. The emergency button 50 may be a component for outputting a message indicating that an emergency occurs through manipulation in a touch manner when the emergency occurs in a human body. That is, when a person physically pushes the emergency button 50, the emergency determination device 1 may transmit a message to an emergency center or an urgent center or may be connected to the emergency center or the center through a wired call. The emergency button may be enabled only when the determiner 200 determines that a mysterious symptom occurs in a person. In this case, the emergency center may include a medical institution, an emergency room, or the like, and the urgent center may include a fire station and a police station. The housing 10 having the emergency determination device 1 installed therein may be disposed adjacent to a general place where a person sleeps. The sensor 100 installed in the housing 10 may recognize the state of a sleeping person.

The sensor 100 may detect a vital sign of a person and a gesture of a human hand 20 within a predetermined range. For example, the sensor 100 may be any one of an impulse-radio ultra wideband (IR-UWB) sensor, Lidar, frequency-modulated continuous-wave (FMCW) radar, and Doppler radar. Ultra wideband (UWB) refers to radio technologies in which a frequency band equal to or greater than 500 MHz is used or a number defined as a fractional band width is equal to or greater than 25%. The fractional band width refers to a bandwidth of a signal compared with a center frequency. Ultra wideband (UWB) refers to radio technologies using a frequency of a broadband and has various advantages such as high range resolution, permeability, robustness with respect to narrowband noise, and coexistence with other devices that share a frequency. For example, ultra wideband communication (UWB) may advantageously detect even minute movement of a target object according to characteristics of super precision range resolution equal to or less than 1 cm.

Impulse-radio ultra wideband (IR-UWB) radar (hereinafter, UWB radar) technologies refer to radar technologies for transmitting an impulse signal of a very short sustainment time having broadband characteristics in a frequency domain and receiving a signal reflected from an object and a person to recognize a surrounding situation through a system configured by applying such ultra wideband communication (UWB) technologies to radar. The UWB radar system generates an impulse signal having a time range of several nanoseconds to several picoseconds through a signal generator and radiates the impulse signal at a wide angle or an angle in a narrow band through a transmission antenna. The radiated signal may be reflected by various objects or people in an environment and the reflected signal may be converted into a digital signal through a reception antenna and an analog-digital converter (ADC).

Lidar may discharge a laser pulse, may receive a signal formed by reflecting the laser pulse back from a surrounding target object, and may measure a distance to the object from the Lidar. The Lidar may detect a speed of the target object, a shape of the target object, or the like as well as the distance to the target object and may also be used to generate a surrounding 3D image.

The vital sign may include at least one of a heart rate, movement, or breathing of a person. The sensor 100 may receive a signal reflected by the person and may detect movement of the chest or abdomen of the person to detect the heart rate or breathing of the person. The sensor 100 may detect whether a current state is sleep apnea through breathing of the person and movement of the heart. Information on breathing of a person and movement of the heart, which are generated in the person in sleep apnea, may be stored in the storage 300.

The sensor 100 may detect movement of a person positioned within a predetermined range and a gesture of the human hand 20. The sensor 100 may receive a reflected signal and may detect movement of the person and the gesture of the human hand 20 in real time. The gesture of the hand 20 may include a specific shape of the hand 20 and a gesture of the hand 20.

For example, the sensor 100 may detect a gesture of the hand 20 that moves within a detection range of the sensor 100. In this case, the gesture of the hand 20 may include a change in distance between the sensor 100 and the hand 20 and a specific motion expressed by the hand 20.

In another example, the sensor 100 may detect the human hand 20 positioned in the detection range of the sensor 100. The sensor 100 may detect the hand 20 positioned in the detection range and may detect a time when the hand 20 stays in the detection range.

In another example, the sensor 100 may detect sudden collapse of a person. The sensor 100 may detect whether the person stands or lies and may detect a change in movement of the person. Thus, the sensor 100 may detect the sudden collapse of the person and may transmit the same to the determiner 200.

The sound recognizer 150 may be a type of the sensor 100 and may detect voice or a specific word of a person. The sound recognizer 150 may detect pre-stored voice or a specific word of the person and may transmit the same to the determiner 200. For example, the voice of the person may refer to pre-stored voice of a specific person, and even if the sound recognizer 150 recognizes non-stored human voice, the sound recognizer 150 may identify that the recognized human voice is not voice of a specific person. For example, the specific word may include "Help!" or the like.

The determiner 200 may analyze at least one of a gesture of the hand 20 or the vital signal, recognized by the sensor 100, and may determine whether an emergency occurs. As the analysis result of the vital sign detected by the sensor 100, when determining that a mysterious symptom occurs in the human body, the determiner 200 may analyze the gesture of the hand 20, detected by the sensor 100, and may determine whether an emergency occurs. The determiner 200 may determine a current state of the person based on information stored in the storage 300. The storage 300 may store various pieces of information on a symptom that occurs in the human body. The information stored in the storage 300 may be classified into information on a mysterious symptom and information on an emergency. That is, the information on the mysterious symptom may include information on the mysterious symptom and the information on the emergency. The information on the emergency may indicate that a more serious problem occurs in the human body compared with the information on the mysterious symptom. For example, the information on the emergency may include apnea of the person, choke in sleep, sleep apnea, inappropriate heartbeat, or the like. That is, the information on the emergency may indicate that a serious problem occurs in a human body to cause a situation in which contact with an emergency center and an urgent center is needed. For example, the information on the mysterious symptom may include information indicating a sudden change in heart rate of the person, unsafe breathing in sleep, or the like. That is, the information on the mysterious symptom may indicate that a problem occurs in a human body but a contact with an emergency center and an urgent center is not immediately needed. Thus, when the sensor 100 detects a symptom matched with the information on the mysterious symptom, the determiner 200 may additionally detect a gesture of the human hand 20. When the sensor 100 detects the symptom corresponding to the information on the emergency, the determiner 200 may determine that the emergency occurs even if a gesture of the human hand 20 is not detected. The emergency button 50 may be enabled when the vital sign detected by the sensor 100 and the information on the mysterious symptom stored in the storage 300 are matched with each other.

When information detected by the sensor 100 and the sound recognizer 150 corresponds to a wake-up behavior, the determiner 200 may analyze the vital sign detected by the sensor 100. The wake-up behavior may be a behavior of enabling the emergency determination device 1. For example, the wake-up behavior may refer to at least one of a hand gesture of the person, a body gesture of the person, voice, or a specific word. For example, when the sound recognizer 150 recognizes pre-stored voice of a specific person, the determiner 200 may determine that the wake-up behavior occurs. In another example, when the sound recognizer 150 recognizes a pre-stored specific word, the determiner 200 may that the wake-up behavior occurs. In another example, when the sensor 100 recognizes pre-stored hand gesture and body gesture of the person, the determiner 200 may determine that the wake-up behavior occurs. For example, when the sensor 100 detects a behavior in which a person collapses and then rolls from side to side, the determiner 200 may determine that information detected by the sensor corresponds to a wake-up behavior. That is, when the information detected by the sensor 100 and the sound recognizer 150 corresponds to a wake-up behavior, the determiner 200 may determine that the emergency occurs in a person. In contrast, when a wake-up behavior is not detected by the sensor 100 and the sound recognizer 150, the determiner 200 may not determine whether the emergency occurs in the person.

When the sensor 100 detects sudden collapse of a person, the determiner 200 may analyze a vital sign and hand gesture of the person. For example, when the information detected by the sensor 100 and the sound recognizer 150 corresponds to a wake-up behavior and the sensor 100 detects sudden collapse of the person, the determiner 200 may analyze the vital sign and the hand gesture of the person. Differently from the aforementioned example, upon detecting the wake-up behavior, the determiner 200 may analyze the vital sign and the hand gesture of the person.

When the sensor 100 detects a vital sign matched with information on a mysterious symptom but does not detect a gesture of the hand 20, matched with a setting condition, within one hour, the determiner 200 may determine that an emergency does not occur. The setting condition may refer to pieces of information on the gesture of the hand 20, stored in the storage 300. That is, the setting condition may refer to gestures of the hand 20, which a person takes in an emergency. For example, the setting condition may include a condition in which a hand is positioned in the detection range of the sensor 100 for a specific time, a condition in which the hand 20 takes a specific gesture within the detection range of the sensor 100, or a condition in which the hand 20 moves a preset number of times at a boundary of the detection range of the sensor 100. When the sensor 100 does not detect a gesture of the hand 20, matched with the setting condition, within a first time, the sensor 100 may repeatedly measure a vital sign of a person. When the repeatedly measured vital sign is continuously matched with information on a mysterious symptom and the sensor 100 does not detect a gesture of the hand 20, matched with the setting condition, within a second time, the determiner 200 may determine that an emergency occurs. The second time may refer to a longer time than the first time. When the vital sign detected by the sensor 100 is matched with the information on the mysterious symptom but the mysterious symptom is generated in the person for a long time, a human body may be seriously hurt. In contrast, when the mysterious symptom is detected only for a short time, a serious problem may not occur in a human body. Thus, when the repeatedly measured vital sign of the person is continuously matched with the information on the mysterious symptom for the second time, the determiner 200 may determine that an emergency occurs.

The information detected by the sensor 100 and the sound recognizer 150 is a sleep behavior, the determiner 200 may determine that an emergency does not occur in a person and may stop analyzing a vital sign and hand gesture of a person. The sleep behavior may refer to at least one of a hand gesture, voice, or a specific word of the person. In this case, the sensor 100 may detect whether the person stands, and the determiner 200 may determine that an emergency does not occur in the person based on the fact that the person stands and sleeps.

The storage 300 may store various pieces of information on a symptom generated in a human body. The information stored in the storage 300 may be classified into information on a mysterious symptom and information on an emergency. The storage 300 may set and store conditions recognized as an emergency among gestures of the hand 20 that a person takes. The storage 300 may store specific gestures of the hand 20 and a specific shape of the hand 20 as the setting condition.

The storage 300 may store information on a wake-up behavior and a sleep behavior. The storage 300 may pre-store a hand gesture, voice, or a specific word of the person, which corresponds to the wake-up behavior. The determiner 200 may match information detected by the sensor 100 and the sound recognizer 150 with information stored in the storage 300 and may determine whether the information detected by the sensor 100 and the sound recognizer 150 is the wake-up behavior or the sleep behavior.

When the determiner 200 determines that an emergency occurs, the communicator 400 may transmit a message that the emergency occurs to a predetermined emergency center or urgent center. The communicator 400 may be connected to the predetermined emergency center or urgent center through a wired call. After the determiner 200 determines that an emergency occurs, the communicator 400 may transmit information on a vital sign of a person to the predetermined emergency center or urgent center in real time. As such, a state in a person in an emergency may be transmitted to the emergency center, the urgent center, or a life saver in real time. When detecting a sleep behavior, the determiner 200 may stop transmitting a message indicating that the emergency occurs. In addition, when the sleep behavior is detected after the message indicating that the emergency occurs, the communicator 400 may transmit a message indicating that an emergency does not occur in the person to the emergency center or the urgent center.

According to an embodiment of the present disclosure, the emergency determination device 1 may detect a current state of the person and may determine whether an emergency currently occurs. The emergency determination device 1 may differentiate between the case in which the person is capable of directly transmitting a signal for help or making a call for help and the case in which the person is not capable of directly transmitting the signal for help or making a call for help. As such, the emergency determination device 1 may contact the emergency center or the urgent center instead of a person in an emergency.

According to an embodiment of the present disclosure, the emergency determination device 1 may detect various symptoms that occur in a person and may identify whether the currently detected symptom is a symptom related to a mysterious symptom or a symptom related to an emergency. As such, a help request may be prevented from being indiscreetly transmitted to the emergency center or the urgent center.

According to an embodiment of the present disclosure, the emergency determination device 1 may detect an emergency that occurs while a person sleeps and may automatically contact the emergency center or the urgent center.

According to an embodiment of the present disclosure, the emergency determination device 1 may be enabled by a wake-up behavior, thereby preventing a state of the person from being misperceived due to a malfunction of the sensor 100.

Figure 3:
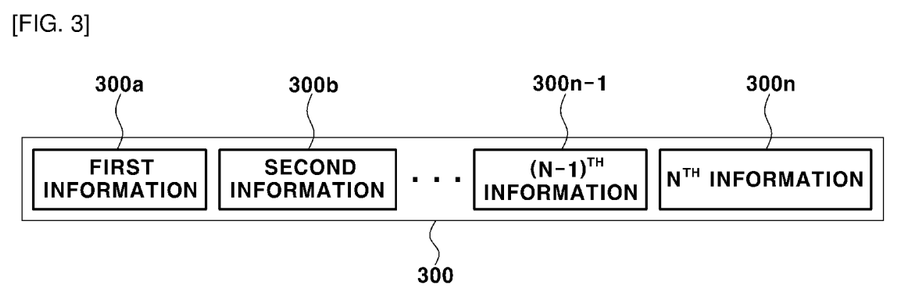
FIG. 3 is a block diagram showing a storage according to an embodiment of the present disclosure.

FIG. 3 is a block diagram showing a storage according to an embodiment of the present disclosure. For simplification of the description, a repeated description is omitted.

Referring to FIGS. 1 to 3, the storage 300 may store various pieces of information on symptoms that occur in a human body and setting conditions that refer to an emergency. The various pieces of information may include pieces of information on a mysterious symptom that occurs in a person and information on an emergency.

For example, the storage 300 may store first information $300a$, second information $300b$, $(n-1)^{th}$ information $300n-1$, and $n^{th}$ information $300n$. The first information $300a$ may include information of the pieces of information on a mysterious symptom, the second information $300b$ may include information of the pieces of information on an emergency, the $(n-1)^{th}$ information $300n-1$ may include information on a specific behavior of the human hand 20, which represents an emergency, and $n^{th}$ information $300n$ may include a gesture of the human hand 20, which represents an emergency.

The storage 300 may store a hand gesture, a body gesture, voice, or a specific word of the person, which corresponds to a wake-up behavior. When information corresponding to the wake-up behavior, stored in the storage 300, is matched with information recognized by the sensor 100 and the sound recognizer 150, the determiner 200 may determine that the wake-up behavior is present.

The determiner 200 may determine whether information matched with a vital sign detected by the sensor 100 and a gesture of the hand 20 are present among the pieces of information stored in the storage 300. The determiner 200 may recognize the current state of the person based on the information matched with the vital sign and the gesture of the hand 20.

Figure 4:
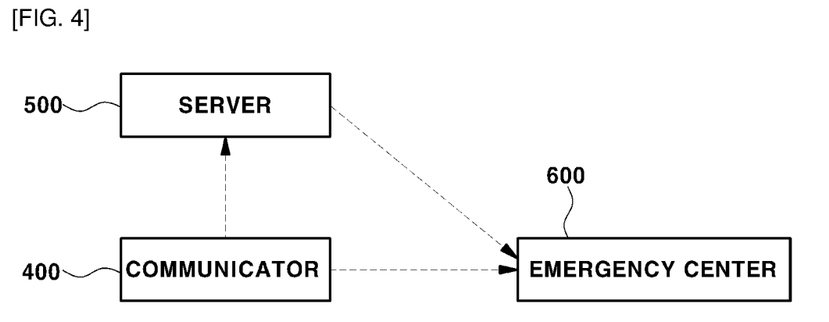
FIG. 4 is a block diagram for explaining a communication method of a communicator according to an embodiment of the present disclosure.

FIG. 4 is a block diagram for explaining a communication method of a communicator according to an embodiment of the present disclosure.

Referring to FIGS. 2 and 4, the communicator 400 may directly transmit a message indicating that an emergency occurs to an emergency center 600 or may be connected thereto through a wired call. The communicator 400 may transmit a message to the emergency center 600 without a separate intermediate server or may be connected to the emergency center 600 through a wired call. The communicator 400 may transmit information on a vital sign by which a current state of a person is capable of being recognized to the emergency center 600.

The communicator 400 may transmit a message indicating that an emergency occurs to the emergency center 600 through a server 500 or may be connected to the emergency center 600 through a wired call. In this case, the server 500 may transmit the analysis result of the vital sign detected by the sensor 100, personal information of the person, or the like to the emergency center 600.

Figure 5:
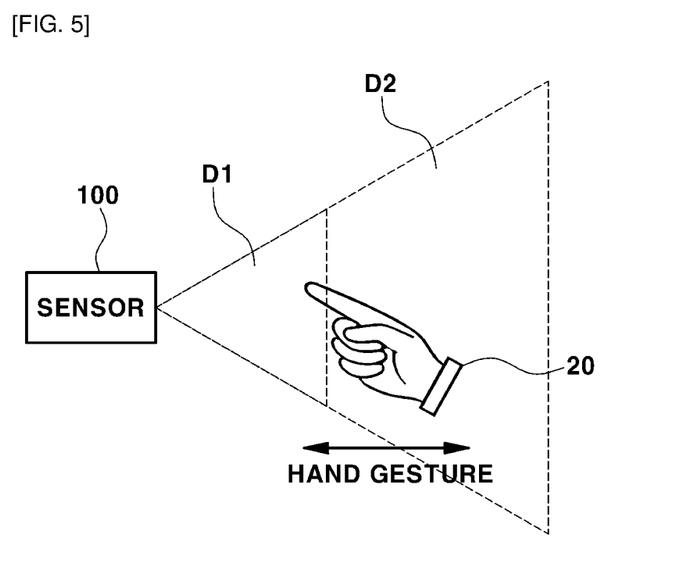
FIG. 5 is a diagram for explaining an example of detection of a hand gesture of a person according to an embodiment of the present disclosure.

FIG. 5 is a diagram for explaining an example of detection of a hand gesture of a person according to an embodiment of the present disclosure. For simplification of the description, a repeated description is omitted.

Referring to FIGS. 2 and 5, the sensor 100 may detect a gesture of the hand 20 positioned with in a detection range. When a vital sign matched with information on the mysterious symptom is detected by the sensor 100, the determiner 200 may analyze a gesture of the hand 20. The detection range of the sensor 100 may include a first detection range D1 and a second detection range D2. For example, the first detection range D1 and the second detection range D2 may not overlap each other. In this case, the first detection range D1 may be set based on a position of the person. For example, the first detection range D1 may be to the sensor 100 from a position spaced part from the person by a specific distance. The second detection range D2 may be to the person from a boundary of the first detection range D1. In another example, the second detection range D2 may include the first detection range D1. That is, the second detection range D2 may include a wider detection range than the first detection range D1.

The hand 20 may be moved between the first detection range D1 and the second detection range D2. Thus, a boundary between the first detection range D1 and the second detection range D2 may be similar to a position of the hand when a person stretches his or her hand. A person in an emergency may swing the hand 20 toward the sensor 100. In this case, the hand 20 may be positioned in the first detection range D1 of the sensor 100 or may also be positioned in the second detection range D2.

For example, when a gesture of the hand 20 is detected within the first detection range D1 a preset number of times by the sensor 100, the determiner 200 may determine that an emergency occurs. The hand 20 may be positioned within the first detection range D1 and may then be moved out of the first detection range D1. That is, as the person swings the hand 20, the sensor 100 may measure a number of times that the hand 20 is detected within the first detection range D1 for a specific time. When the hand 20 is detected within the first detection range D1 a preset number of times for the specific time, the determiner 200 may determine that an emergency occurs in the person.

In another example, when the sensor 100 detects that the human hand 20 is moved to the first detection range D1 from the second detection range D2 a preset number of times or greater within a preset time, the determiner 200 may determine that an emergency occurs. That is, the sensor 100 may measure a number of times that the hand 20 is moved to the first detection range D1 from the second detection range D2 for a specific time through a behavior in which the person swings the hand 20.

The gestures of the hand 20 in the aforementioned examples may be stored as a setting condition in the storage 300.

Differently from the aforementioned example, the sensor 100 may detect a specific gesture that a human hand takes. The specific gesture may be stored in the storage 300. Thus, when the specific gesture of the hand is detected within a detection range, the determiner 200 may determine that an emergency occurs in the person.

Figure 6:
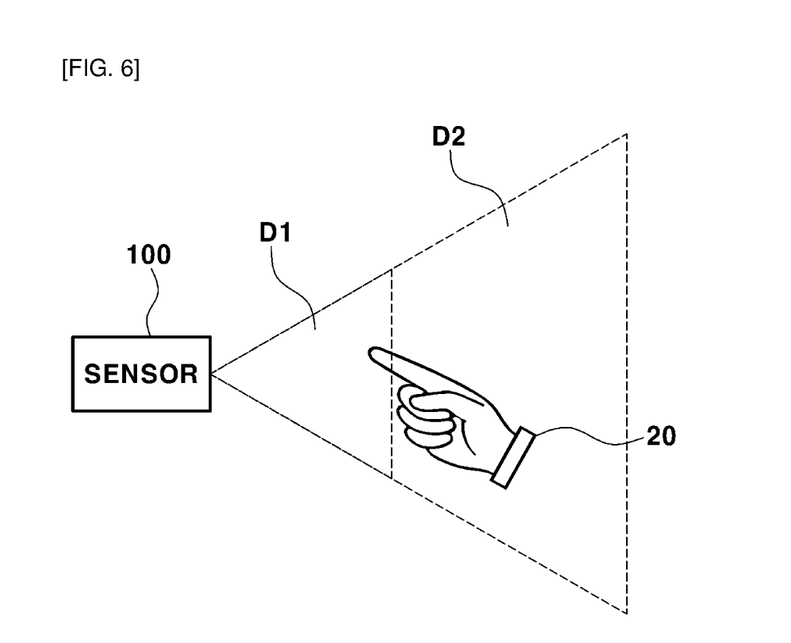
FIG. 6 is a diagram for explaining another example of detection of a hand gesture of a person according to an embodiment of the present disclosure.

FIG. 6 is a diagram for explaining another example of detection of a hand gesture of a person according to an embodiment of the present disclosure. For simplification of the description, a repeated description is omitted.

Referring to FIGS. 2 and 6, the sensor 100 may detect a detection range in which the hand 20 is positioned, from the first detection range D1 or the second detection range D2. For example, when the sensor 100 continuously detects the hand 20 within the first detection range D1 for a preset time, the determiner 200 may determine that an emergency occurs. When the emergency occurs, the person may stretches his or her hand toward the sensor 100. When the hand is stretched toward the sensor 100, the hand 20 may be detected within the first detection range D1. The first detection range D1 may refer to a range detected by the sensor 100 when the person intentionally stretches the hand 20 toward the sensor 100. The preset time may refer to a time in which it is difficult to continuously detect the human hand 20 in a daily life. Thus, when the hand 20 is detected for a preset time within the first detection range D1, the determiner 200 may recognize that an abnormal situation occurs. When the sensor 100 detects a vital sign matched with information on a mysterious symptom, the determiner 200 may analyze a gesture of the hand 20.

Figure 7:
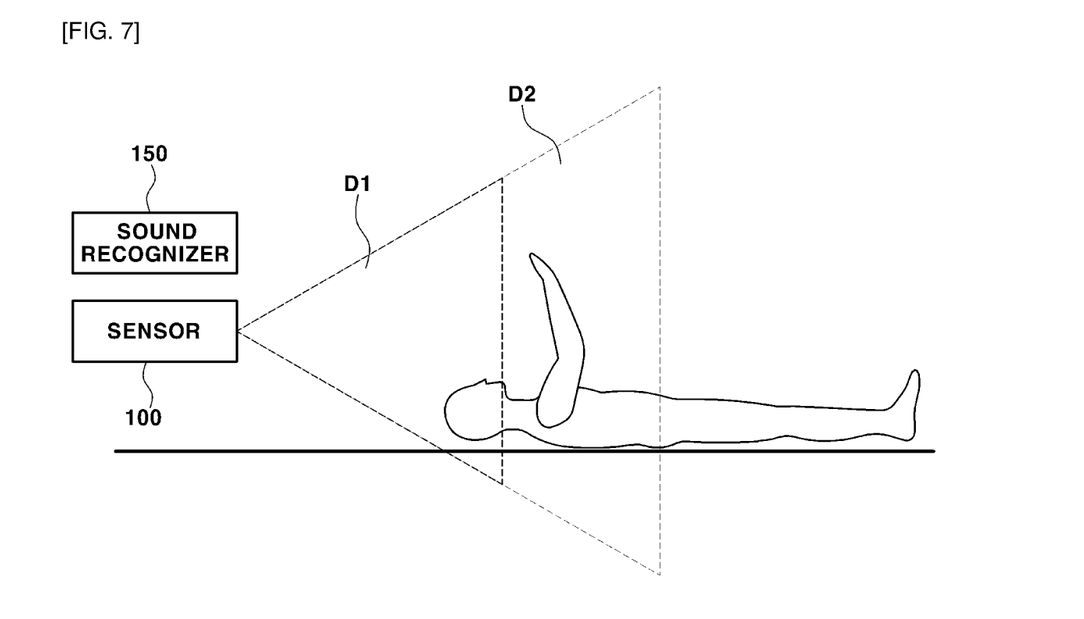
FIG. 7 is a diagram for explaining detection of an emergency according to an embodiment of the present disclosure.

FIG. 7 is a diagram for explaining detection of an emergency according to an embodiment of the present disclosure. For simplification of the description, a repeated description is omitted.

Referring to FIGS. 2 and 7, the sensor 100 may detect sudden collapse of a person. The sensor 100 may detect whether a wake-up behavior occurs and a specific hand gesture that the person takes after the sudden collapse of the person. In this case, the wake-up behavior may also be detected by the sound recognizer 150.

After the sudden collapse, the person may do the wake-up behavior in order to enable the emergency determination device 1. For example, the wake-up behavior may include a behavior to be also done by the person who suddenly collapses, a behavior in which the person continuously claps his or her hands, or a behavior in which the person utters a specific word through specific voice. The sensor 100 may detect the behavior in which the person continuously claps his or her hands or the sound recognizer 150 may detect sound generated by the specific word, the specific voice, and a clapping sound.

When the determiner 200 determines that the wake-up behavior is present, the sensor 100 may detect the specific hand gesture that the person takes and the vital sign of the person. In detail, as the analysis result of the vital sign detected by the sensor 100, when determining that a mysterious symptom occurs in the human body, the determiner 200 may analyze the gesture of the hand, detected by the sensor 100, and may determine whether an emergency occurs. The method of recognizing a hand gesture has been described above with reference to FIGS. 5 and 6, and thus, will not be described below.

Figure 8:
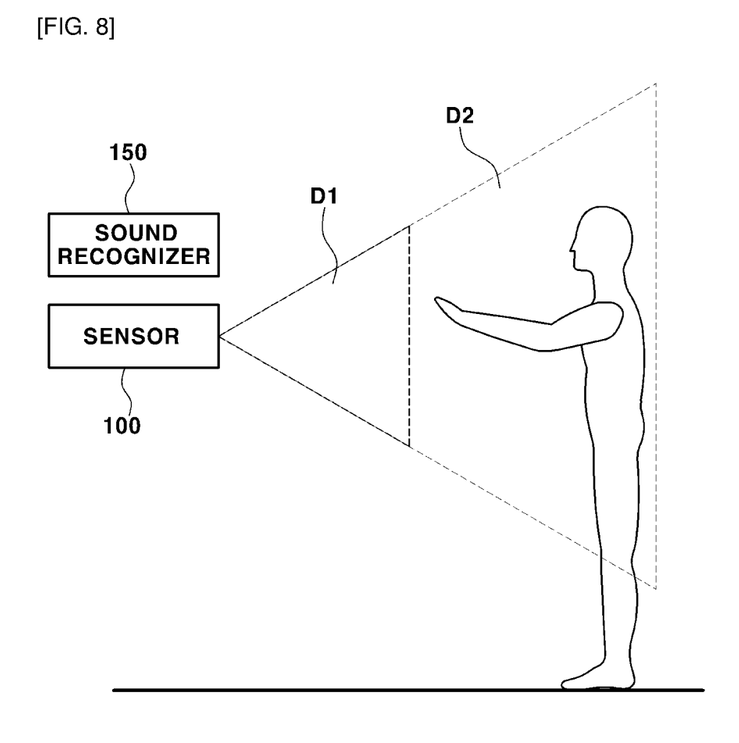
FIG. 8 is a diagram for explaining a sleep behavior according to an embodiment of the present disclosure.

FIG. 8 is a diagram for explaining a sleep behavior according to an embodiment of the present disclosure.

Referring to FIGS. 2 and 8, the sensor 100 and the sound recognizer 150 may detect a sleep behavior, and when the sleep behavior is detected, the determiner 200 may stop analyzing a vital sign and hand gesture of a person. The sensor 100 may detect whether a person does the sleep behavior while standing. For example, the sleep behavior may be different from the wake-up behavior. For example, the person may swing his or her hand while standing, and the determiner 200 may determine a standing behavior and a hand swing behavior of the person as the sleep behavior.

Figure 9:
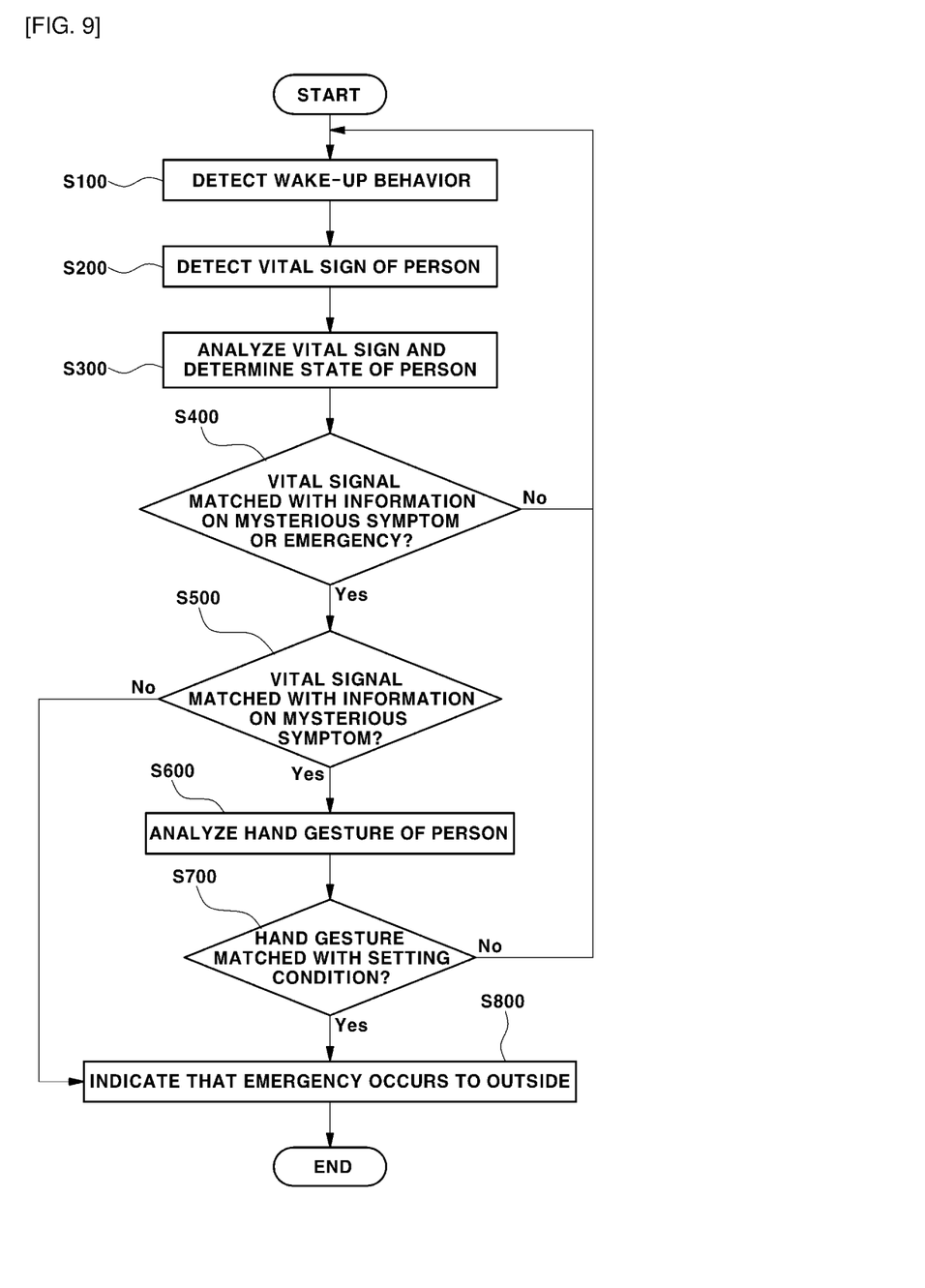
FIG. 9 is a flowchart for explaining a method of determining an emergency according to an embodiment of the present disclosure.

FIG. 9 is a flowchart for explaining a method of determining an emergency according to an embodiment of the present disclosure. For simplification of the description, a repeated description is omitted.

Referring to FIG. 9, the sensor and the sound recognizer may detect the wake-up behavior. For example, the wake-up behavior may include a behavior to be also done by the person who suddenly collapses, a behavior in which the person continuously claps his or her hands, or a behavior in which the person utters a specific word through specific voice. After the wake-up behavior is detected, the emergency determination device may be enabled. When the emergency determination device is enabled, this means that the determiner analyzes the vital sign detected by the sensor and a hand gesture of the person (S100).

The sensor may detect a vital sign of the person. The sensor may be disposed at a place adjacent to a person, and in detail, may be installed at a place where the person sleeps (S200).

The determiner may analyze the vital sign detected by the sensor and may determine the state of the person. The determiner may match information on various symptoms that occur in the person, which is stored in a storage, with the vital sign detected by the sensor. As such, the determiner may determine the meaning of the vital sign detected by the sensor, and may determine whether the symptom that occurs in the person is related to a mysterious symptom or an emergency (S300).

The determiner may determine information that is matched with the vital sign among the information on the mysterious symptom and the information on the emergency. When the vital sign is not matched with the information on the mysterious symptom and the information on the emergency, the determiner may determine that the state of the person is stable (S400).

When the vital sign is matched with the information on the mysterious symptom, the determiner may analyze a hand gesture (S500 and S600).

However, when the vital sign is not matched with the information on the mysterious symptom, the vital sign may be matched with the information on the emergency, and thus, the determiner may recognize that the state of the person is in an emergency. In this case, a communicator may indicate that the emergency occurs to the outside (S800).

When the vital sign is matched with the information on the mysterious symptom, the determiner may determine whether the hand gesture is matched with a setting condition. The setting condition may include information on a hand gesture of the person, by which an emergency is to be recognized. That is, the determiner may analyze the hand gesture and may recognize whether the person wants a help request. When the hand gesture is not matched with the setting condition, the sensor may repeatedly detect the vital sign of the person. The sensor may detect the vital sign of the person in real time, and the determiner may analyze the vital sign in real time. However, even if the hand gesture is not matched with the setting condition, the vital sign matched with the information on the mysterious symptom is detected from the person for a predetermined time or more, the determiner may determine that an emergency occurs in the person (S700).

When the determiner determines that an emergency occurs, the communicator may indicate that the emergency occurs to the outside. After the determiner determines that the emergency occurs, when the sensor detects a sleep behavior, the communicator may transmit a message indicating that an emergency does not occur in a person or is resolved to an emergency center or an urgent center. When the sensor detects the sleep behavior, the emergency determination device may be initiated. When the emergency determination device is initiated, this means that analysis of the vital sign and the hand gesture that have been detected up to now is analyzed (S800).

According to an embodiment of the present disclosure, the emergency determination device may detect a current state of the person and may determine whether an emergency currently occurs. As such, the emergency determination device may contact the emergency center or the urgent center instead of a person in an emergency.

According to an embodiment of the present disclosure, the emergency determination device may detect various symptoms that occur in a person and may identify whether the currently detected symptom is a symptom related to a mysterious symptom or a symptom related to an emergency. As such, a help request may be prevented from being indiscreetly transmitted to the emergency center or the urgent center.

According to an embodiment of the present disclosure, the emergency determination device may detect an emergency that occurs while a person sleeps and may automatically contact the emergency center or the urgent center.

According to an embodiment of the present disclosure, the emergency determination device may be enabled by a wake-up behavior, thereby preventing a state of the person from being misperceived due to a malfunction of the sensor.

The present disclosure has been described in detail with reference to preferred embodiments thereof. However, it will be appreciated by those skilled in the art that changes may be made in these embodiments without departing from the principles and spirit of the present disclosure, the scope of which is defined in the appended claims and their equivalents.

What is claimed is:

1. An emergency determination device for determining whether an emergency occurs, comprising:
    a sensor configured to detect a vital sign of a person and a hand gesture of the person within a predetermined range; and
    a determiner configured to analyze the vital sign recognized by the sensor, to additionally analyze the hand gesture based on a result obtained by analyzing the vital sign, and to determine whether the emergency occurs,
    wherein the determiner analyzes the vital sign and determines whether the emergency occurs after the sensor detects a wake-up behavior;
    wherein the wake-up behavior is a behavior for enabling the emergency determination device; and
    wherein, when the sensor detects a sleep behavior, the determiner determines that the emergency does not occur in the person and stops analyzing the vital sign of the person and analyzing the hand gesture.

2. The emergency determination device of claim 1, wherein the wake-up behavior includes at least one of the hand gesture of the person, a body gesture of the person, voice, or a specific word.

3. The emergency determination device of claim 1, wherein the sensor detects the vital sign after detecting the wake-up behavior and detecting collapse of the person.

4. The emergency determination device of claim 1, wherein, when determining that a mysterious symptom is present in a body of the person as a result obtained by analyzing the vital sign detected by the sensor, the determiner analyzes the hand gesture detected by the sensor and determines whether the emergency occurs.

5. The emergency determination device of claim 4, wherein the sensor detects the hand gesture within a first detection range and a second detection range; wherein, when the sensor detects the hand gesture of the person within the first detection range a preset number of times or more, the determiner determines that the emergency occurs; and wherein the first detection range is narrower than the second detection range.

6. The emergency determination device of claim 5, wherein, when the sensor detects that a hand of the person moves to the first detection range from the second detection range within a predetermined time a preset number of times or more, the determiner determines that the emergency occurs.

7. The emergency determination device of claim 1, wherein the determiner includes a storage configured to store various pieces of information on a symptom generated in a body of the person; and wherein the pieces of information is classified into information on a mysterious symptom and information on the emergency.

8. The emergency determination device of claim 7, wherein, when the vital sign measured by the sensor is matched with the information on the mysterious symptom, the determiner detects the hand gesture and determines whether the emergency occurs.

9. The emergency determination device of claim 8, wherein, when the sensor does not detect the hand gesture matched with a setting condition for a first time, the sensor repeatedly measures the vital sign.

10. The emergency determination device of claim 9, wherein, when the vital sign that is repeatedly measured is continuously matched with the information on the mysterious symptom and the sensor does not detect the hand gesture matched with the setting condition for a second time, the determiner determines that the emergency occurs; and wherein the second time is longer than the first time.

11. The emergency determination device of claim 7, wherein, when the vital sign measured by the sensor is matched with the information on the emergency, even if the hand gesture is not detected, the determiner determines that the emergency occurs.

12. The emergency determination device of claim 1, further comprising:
a communicator configured to transmit a message indicating that the emergency occurs to a predetermined emergency center or urgent center when determining that the emergency occurs.

13. The emergency determination device of claim 12, wherein, after the determiner determines that the emergency occurs, the communicator transmits information on the vital sign of the person to the predetermined emergency center or the urgent center in real time.

14. The emergency determination device of claim 1, further comprising:
an emergency button configured to indicate that the emergency occurs to the outside, wherein the emergency button is enabled when the determiner determines that a mysterious symptom is generated in the person.

15. An emergency determination device for determining whether an emergency occurs, comprising:

a sensor configured to detect a vital sign of a person and a hand gesture of the person within a predetermined range; and
a determiner configured to analyze the vital sign recognized by the sensor, to additionally analyze the hand gesture based on a result obtained by analyzing the vital sign, and to determine whether the emergency occurs,
wherein the determiner analyzes the vital sign and determines whether the emergency occurs after the sensor detects a wake-up behavior;
wherein the wake-up behavior is a behavior for enabling the emergency determination device;
wherein, when the sensor detects a sleep behavior, the determiner determines that the emergency does not occur in the person and stops analyzing the vital sign of the person and analyzing the hand gesture;
wherein, when determining that a mysterious symptom is present in a body of the person as a result obtained by analyzing the vital sign detected by the sensor, the determiner analyzes the hand gesture detected by the sensor and determines whether the emergency occurs;
wherein the sensor detects the hand gesture within a first detection range and a second detection range;
wherein, when the sensor detects the hand gesture of the person within the first detection range a preset number of times or more, the determiner determines that the emergency occurs; and
wherein the first detection range is narrower than the second detection range.

* * * * *